United States Patent
Luterbacher et al.

(10) Patent No.: US 10,906,856 B2
(45) Date of Patent: Feb. 2, 2021

(54) PRODUCTION OF MONOMERS FROM LIGNIN DURING DEPOLYMERIZATION OF LIGNOCELLULOSE-CONTAINING COMPOSITION

(71) Applicant: Ecole Polytechnique Federale de Lausanne (EPFL), Lausanne (CH)

(72) Inventors: Jeremy Scott Luterbacher, Chavannes-Renens (CH); Li Shuai, Lausanne (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 16/093,065

(22) PCT Filed: Apr. 12, 2017

(86) PCT No.: PCT/EP2017/058743
§ 371 (c)(1),
(2) Date: Oct. 11, 2018

(87) PCT Pub. No.: WO2017/178513
PCT Pub. Date: Oct. 19, 2017

(65) Prior Publication Data
US 2019/0127304 A1    May 2, 2019

(30) Foreign Application Priority Data
Apr. 13, 2016 (EP) .................... 16165180

(51) Int. Cl.
*C07C 41/01* (2006.01)
*C07G 1/00* (2011.01)
*C08B 37/00* (2006.01)
*C08H 7/00* (2011.01)
*D21C 11/00* (2006.01)

(52) U.S. Cl.
CPC .............. *C07C 41/01* (2013.01); *C07G 1/00* (2013.01); *C08B 37/0057* (2013.01); *C08H 6/00* (2013.01); *D21C 11/0007* (2013.01)

(58) Field of Classification Search
CPC .................................................. D21C 11/0007
See application file for complete search history.

(56) References Cited

U.S. PATENT DOCUMENTS

| | | | |
|---|---|---|---|
| 2,760,861 A | 8/1956 | Furman et al. | |
| 3,617,435 A | 11/1971 | Kalisch | |
| 3,711,366 A | 1/1973 | Nakano et al. | |
| 4,281,063 A * | 7/1981 | Tsao | C12N 9/2434 127/37 |
| 5,433,825 A * | 7/1995 | Minor | D21C 1/06 162/78 |
| 5,730,837 A | 3/1998 | Black et al. | |
| 6,464,827 B1 | 10/2002 | Colodette | |
| 2011/0071306 A1* | 3/2011 | Robinson | C07C 43/137 549/488 |
| 2011/0268652 A1 | 11/2011 | Machhammer et al. | |
| 2012/0122152 A1* | 5/2012 | Blackbourn | C13K 1/04 435/41 |
| 2012/0202260 A1* | 8/2012 | Maclachlan | C01B 3/50 435/157 |
| 2013/0305594 A1* | 11/2013 | Shuai | C10L 1/04 44/330 |
| 2016/0024712 A1* | 1/2016 | Smit | C12P 19/02 435/105 |
| 2016/0102113 A1* | 4/2016 | Jansen | C07G 1/00 44/436 |
| 2016/0102285 A1* | 4/2016 | Pylkkanen | C12M 45/09 435/274 |
| 2016/0130408 A1* | 5/2016 | Jansen | C08H 6/00 514/777 |
| 2016/0152779 A1* | 6/2016 | Pylkkanen | C08H 8/00 435/99 |
| 2016/0185809 A1* | 6/2016 | Streffer | C08H 6/00 530/507 |
| 2017/0152278 A1* | 6/2017 | Samec | C10G 1/002 |
| 2017/0247834 A1* | 8/2017 | Bozell | D21C 3/20 |
| 2018/0030555 A1* | 2/2018 | Van Tuel | C07G 1/00 |
| 2018/0037963 A1* | 2/2018 | Kavakka | B01D 11/04 |
| 2019/0144590 A1* | 5/2019 | Epps, III | C08F 293/005 429/308 |

FOREIGN PATENT DOCUMENTS

| CN | 103508858 | 1/2014 |
|---|---|---|
| WO | 2015/009145 | 1/2015 |

OTHER PUBLICATIONS

Taherzadeh et al. (Ind. Eng. Chem. Res. 1997, 36, 4659-4665) (Year: 1997).*
Search Report and Written Opinion, dated Jul. 18, 2017, corresponding to International Application No. PCT/EP2017/058743 (filed Apr. 12, 2017), parent of the present application, 15 pp.
Shuai et al. (2016) "Formaldehyde Stabilization Facilitates Lignin Monomer Production During Biomass Depolymerization," Science 354(6310):329-333.
Shuai et al. (2016) "Organic Solvent Effects in Biomass Conversion Reactions," Chem Sus Chem 9:133-155.
XP 002762149 (May 30, 1988) WPI Database, Abstract, Thomson Scientific, London, GB.

* cited by examiner

Primary Examiner — Liam J Heincer
(74) Attorney, Agent, or Firm — Leydig, Voit & Mayer, Ltd.

(57) ABSTRACT

The present invention relates to a method for preparing monomers via depolymerisation from lignocellulose-containing biomass.

18 Claims, 6 Drawing Sheets

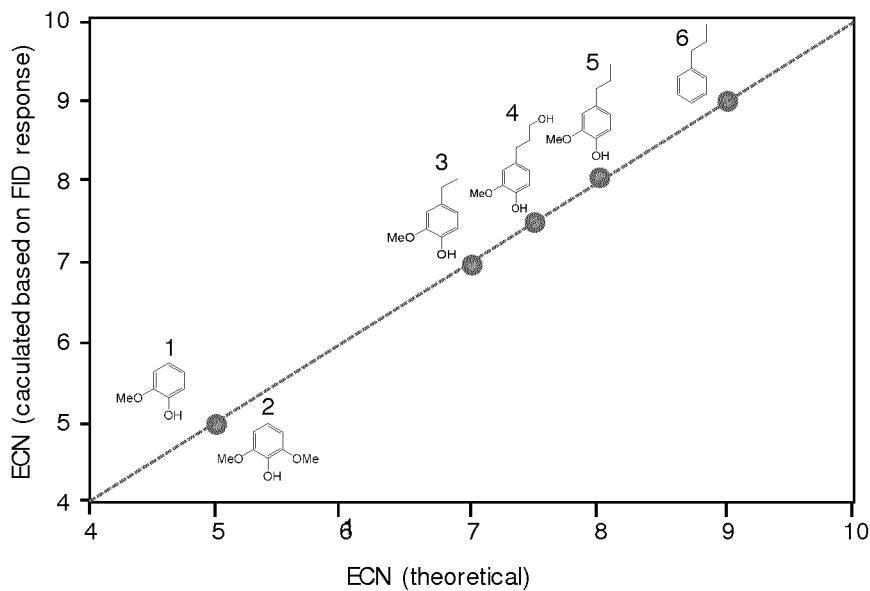

Fig. 1: Validation of Effective Carbon Number (ECN) rule for lignin monomer quantification (X axis: ECN based on empirical rule (Table S3); Y axis: ECN calculated based on FID response using decane as an internal standard). Compound 1 (guaiacol), compound 2 (syringol), compound 3 (guaiacylethane), compound 4 (guaiacylpropanol), compound 5 (guaiacylpropane) and compound 6 (propylbenzene).

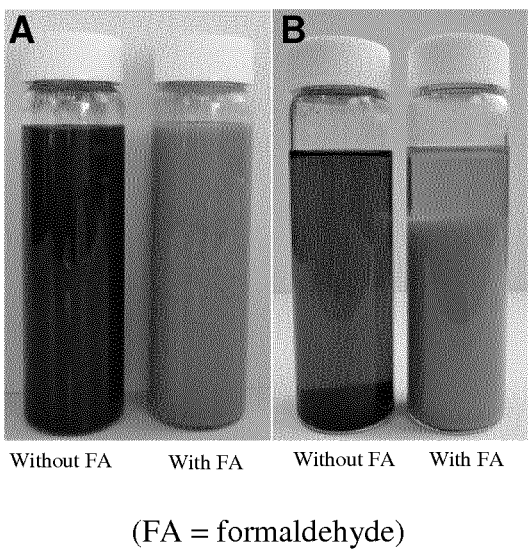

(FA = formaldehyde)

Fig. 2: Precipitation of lignin by adding water into the pretreatment liquors; (A) 0 h after the addition of water, and (B) 15 h after the addition of water. (The dark color suggests a severe condensation of lignin; the light color suggests limited condensation in lignin)

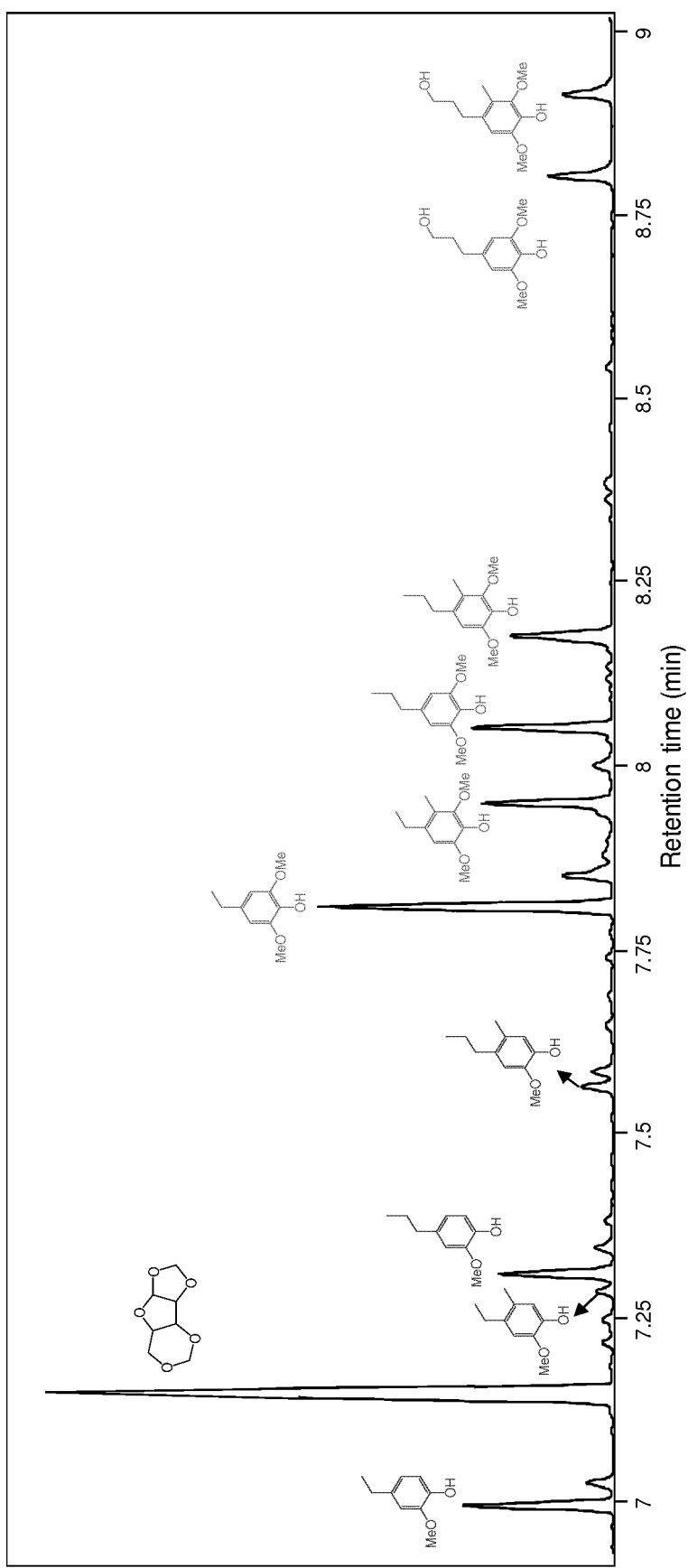
Fig 3a: GC chromatogram of lignin monomers obtained by the method according to the present invention

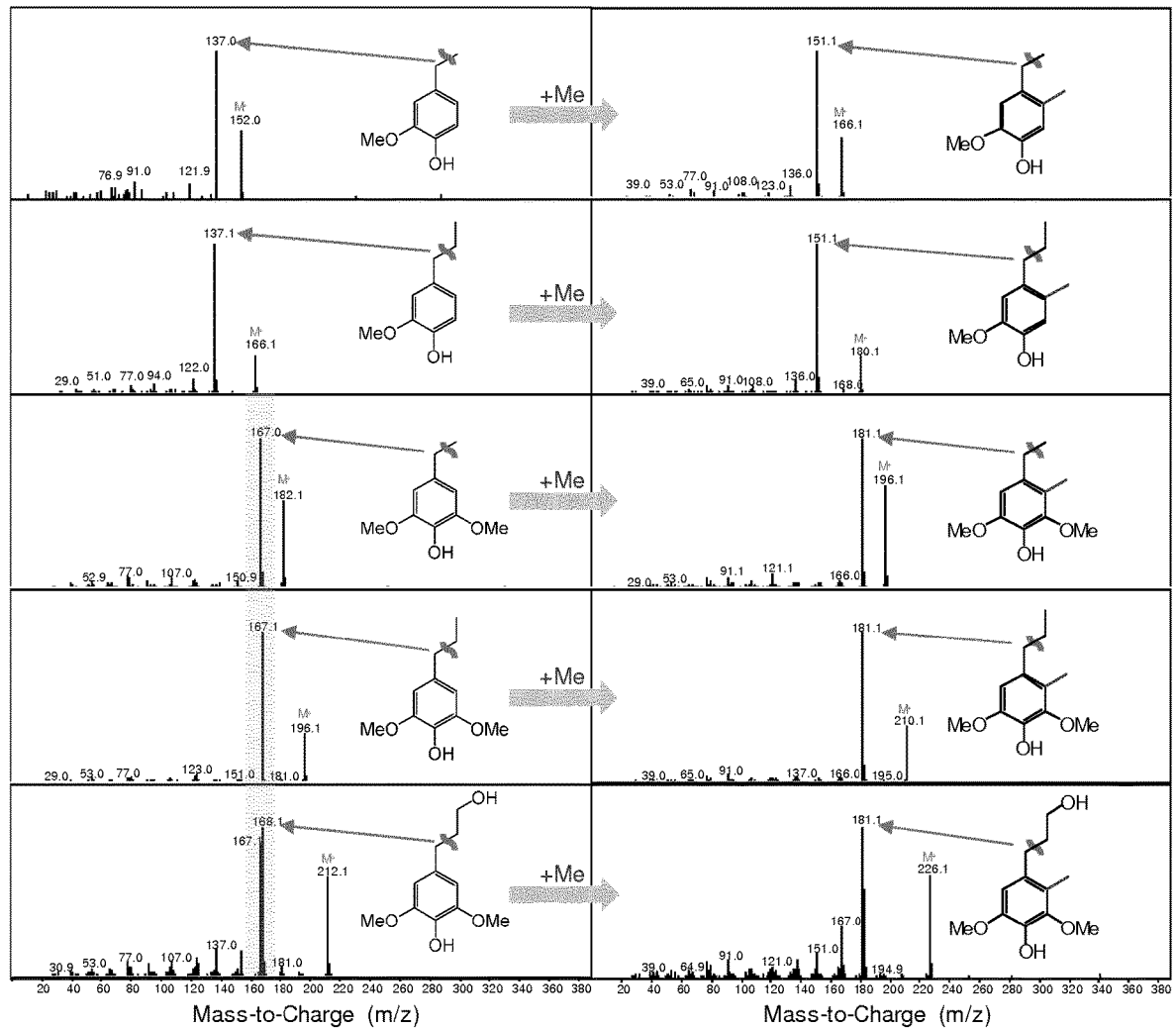
Fig. 3b: Corresponding mass spectra of the lignin monomers obtained by the method according to the present invention.($M^+$ is the molecular ion peak, representing the molecular weight of lignin monomers; the highest peak with red arrow pointed represents the molecular weight of the most stabilized fragment ion from each lignin monomer)

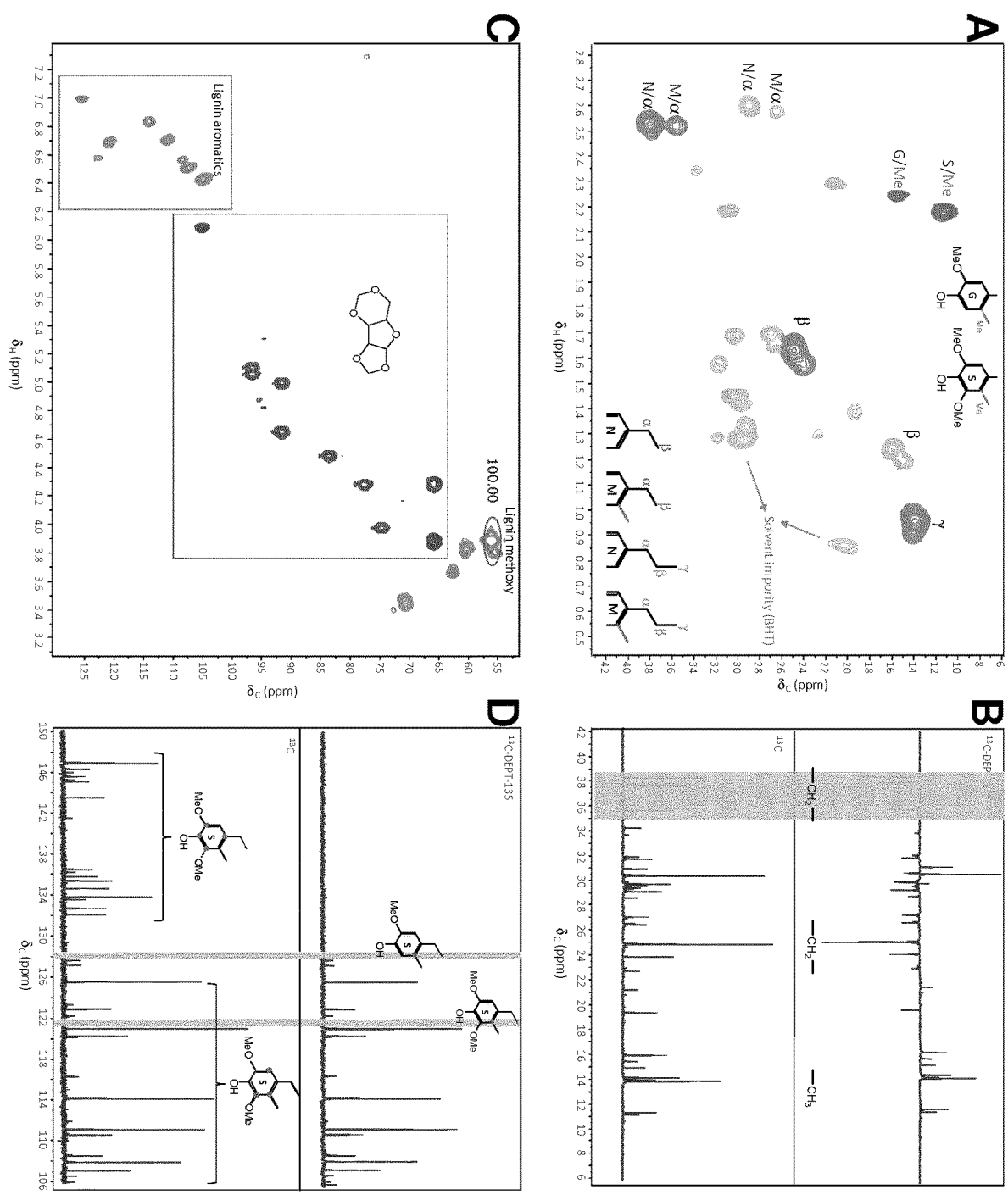

Fig. 4: NMR characterization of hexane-extracted lignin monomers. (A) 2D HSQC NMR spectra (the side chain region of lignin monomers), (B) $^{13}$C and $^{13}$C-DEPT NMR spectra (the side chain region of lignin monomers), (C) 2D HSQC NMR spectra (the aromatic region and methoxy region of lignin monomers), and (D) $^{13}$C and $^{13}$C-DEPT NMR spectra (the side chain region of lignin monomers). The appearance of methyl group in Figure 4A (red) and 4B and tertiary carbon (121 and 128 ppm) in Figure 4D proved the reaction of lignin aromatic ring with formaldehyde.

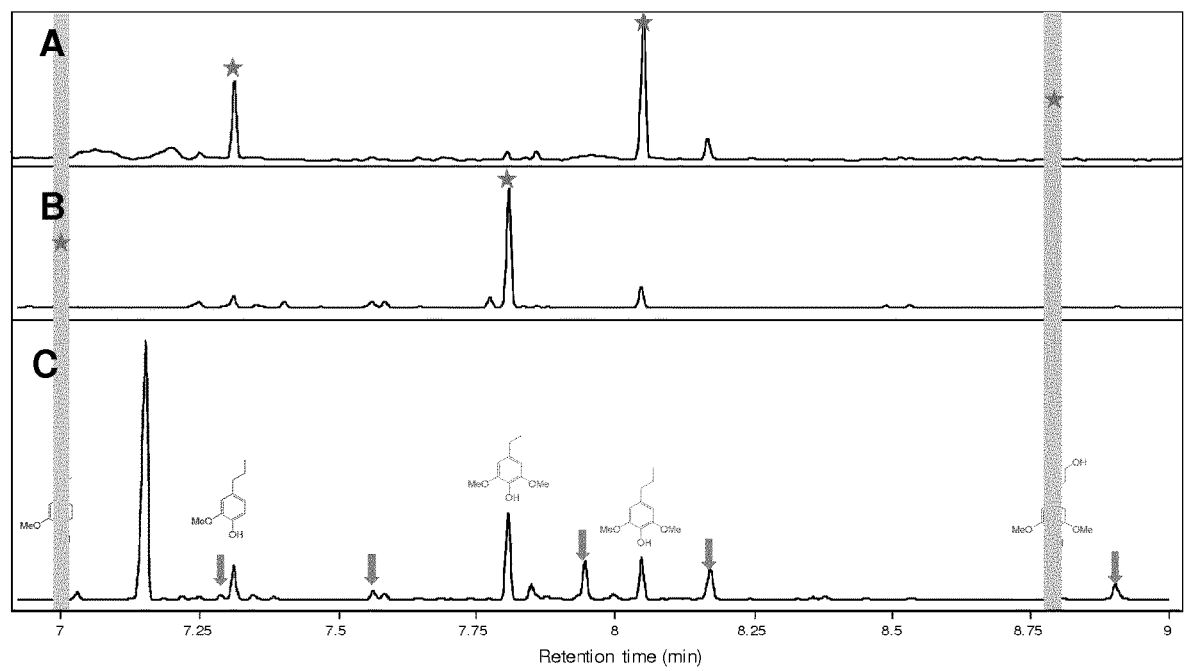

Fig. 5: Comparison of monomers from lignin from different processes; (A) Reference Example R.E. 2.2, (B) Reference Example R.E. 2.2, and (C) Example 2.1. Direct hydrogenolysis of native lignin (A and B) generated five major lignin monomers (highlighted with star); the peaks highlighted with arrow refer to the lignin monomers with methyl group on the aromatic ring which derived from the reaction of lignin monomeric units with FA)

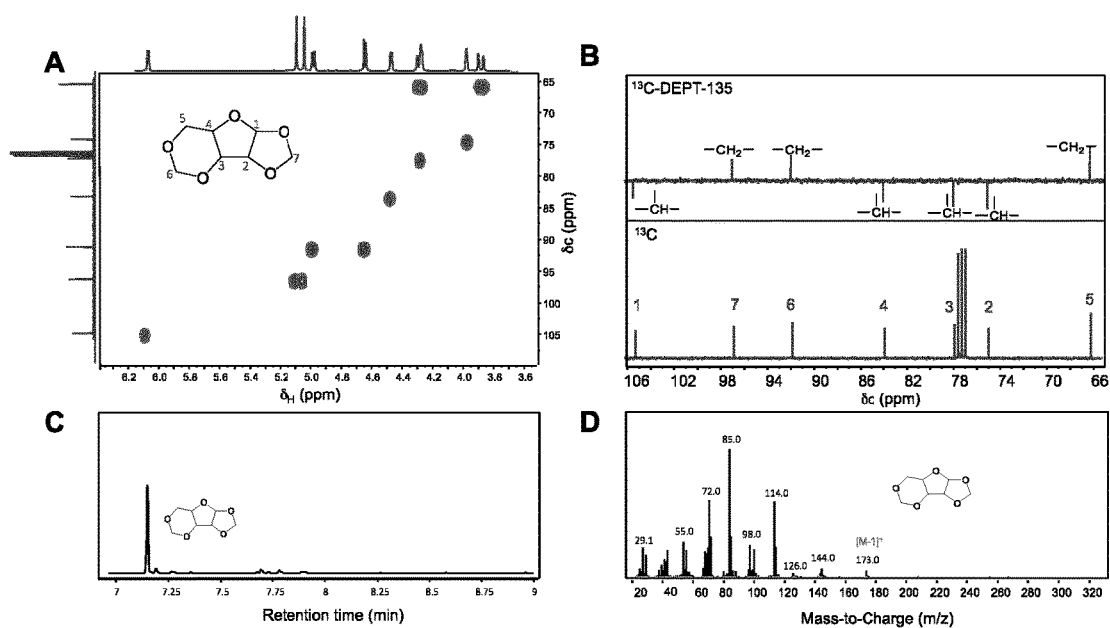
Fig. 6: Identification of diformyl-xylose. (A) 2D HSQC NMR spectra of purified diformyl-xylose, (B) $^{13}$C and $^{13}$C-DEPT-135 NMR spectra of diformyl-xylose, (C) GC chromatogram of diformyl-xylose, and (D) mass spectra of diformyl-xylose.

PRODUCTION OF MONOMERS FROM LIGNIN DURING DEPOLYMERIZATION OF LIGNOCELLULOSE-CONTAINING COMPOSITION

CROSS-REFERENCE TO RELATED APPLICATIONS

This application is a U.S. National Stage Application filed under 35 U.S.C. § 371 of International Application No. PCT/EP2017/058743, filed Apr. 12, 2017, which claims the benefit of European Application No. EP 16165180.7, filed Apr. 13, 2016. Both of these applications are hereby incorporated by reference in their entireties.

The present invention relates to a method for producing monomers via depolymerisation from lignocellulose-containing composition.

BACKGROUND OF THE INVENTION

Lignin is reported to be the second most abundant natural polymer on earth after cellulose, accounting for 15-30 wt. % of lignocellulosic biomass and about 30% of the organic carbon present in the biosphere. Unlike cellulose and hemicellulose, the two other major constituents of lignocellulosic biomass, lignin is not a polysaccharide. Instead, lignin is said to contain a significant amount of aromatic subunits. This structure imparts lignin with an energy density that is 30% higher than cellulosic polymers and makes it one of the few natural sources of aromatic molecules. Because of these properties, lignin monomers are increasingly recognized as an essential precursor for producing renewable aromatic chemicals and/or drop-in fuels.

However, in spite of a longstanding interest in lignin upgrading there are very few commercial processes. This is due to the lack of a practical high-yield lignin depolymerization method that can be integrated with the upgrading of the polysaccharide fractions of biomass.

S. Van den Bosch et al.: "Reductive lignocellulose fractionation into soluble lignin-derived phenolic monomers and dimers and processable carbohydrate pulps", Energy Environ. Sci. 8, 1748-1763 (2015) describes that one of the most prevalent lignin depolymerization strategies is the direct hydrogenolysis of native lignin in biomass. This process is reported to lead to the most frequent lignin monomers, namely the guaiacyl and syringyl subunits. However, after hydrogenolysis this process involves a solid/solid separation step, namely the separation of solid heterogeneous metal catalyst from solid cellulose and hemicellulose residues (polysaccharide fraction). Such a separation is reported to be impractical at an industrial scale due to catalyst recovery and deactivation issues and its incompatibility with leading biorefinery strategies. Furthermore, harsh hydrogenolysis conditions generally lead to a loss of the hemicellulose and some of the cellulose fraction or to their conversion to sugar alcohols. Though these alcohols can be valuable, they cannot be upgraded biologically or converted to furans, which are two major biorefining routes. In addition the direct hydrogenolysis leads to little diversity of monomers.

Hydrogenolysis on "extracted" lignin would avoid many of these issues by allowing separate processing of the polysaccharide and lignin fractions of biomass and the continuous processing of solubilized lignin in flow conditions with heterogeneous catalysts. Promising biorefinery fractionation (or pretreatment) processes, such as those using water, an organic solvent such as alcohol, THF or γ-valerolactone (GVL), ionic liquids (IL), pretreatment, and non-enzymatic GVL-based saccharification, often use high temperatures and/or inexpensive mineral acids (e.g. $H_2SO_4$ and HCl) that facilitate the removal of lignin from cellulose and hemicellulose. A large-scale source of lignin is described to come from a process using these technologies. However, such a use of acid and/or high temperature might lead to severe and irreversible condensation of lignin during its extraction, which dramatically affects its further upgrading. Specifically, it is reported that lignin ether bonds are cleaved at extraction conditions, which often leads to a subsequent formation of highly stable C—C bonds. The mechanism is thought to involve the formation of a highly reactive carbocation at the α-position of the lignin side, which reacts with the negatively-charged positions that are stabilized by methoxy groups on the aromatic rings of lignin units.

Due to the aforementioned condensation, hydrogenolysis of extracted lignin leads to a yield of about 5-20% on a molar basis, wherein this yield is typically 5-10 times lower than the one obtained from native lignin.

US 2011/268652 A1 relates to a method for producing cellulose and at least one low-molecular-weight reusable material, in which a starting material containing lignocellulose is provided and subjected to a decomposition with a processing medium.

CN 103 508 858 A relates to a method for preparing aromatic compounds employing direct catalytic cracking of industrial lignins under a catalytic system with reducing capacity.

WO 2015/009145 A1 relates to a method for fractionating lignocellulosic biomass for the purpose of reducing processing costs, increasing delignification, reducing side-reactions, in particular reducing hemicelluloses degradation, improving cellulose hydrolysis and increasing the nativity of the obtained lignin, by performing fractionation of the biomass with a treatment liquid at a temperature below 170° C.

U.S. Pat. No. 2,760,861 A relates to a method for the separation and recovery of cellulose and lignin from lignin-containing cellulosic materials.

Consequently, there is a need for a method for the production of monomers from lignin which can be applied in a simple and effective manner and which preferably is compatible with the common biorefinery strategies.

Hence, it was an object of the present invention to overcome the drawbacks of the above-mentioned processes.

In particular, it was an object of the present invention to provide a method for the production of monomers from lignin with an advantageous yield, even when used in a large scale process. Further said method should be compatible with common biorefinery strategies, which allows biological upgrade or conversion to furan of the hemicellulose/cellulose fraction.

In particular, methods including harsh reaction conditions should be avoided. Further, methods including a solid/solid separation, especially after hydrogenolysis, should be avoided.

A method providing a high yield of monomers of lignin should be provided, wherein harsh reactions can be avoided and which is compatible with common biorefinery processes.

Additionally, a method for the production of fragments of hemicellulosic compounds and the monomer thereof should be provided.

It was a further object of the invention to provide a method for the production of lignin monomers, wherein expensive and/or so called "sophisticated" compounds, such as enzyme-based agents, should be avoided.

According to the present invention, the above objectives are achieved by the specific method as described herein for the production of monomers from lignin.

SUMMARY

The present invention has unexpectedly solved the above objectives by the provision of a new method for producing monomers from lignin via depolymerisation. In particular, a method including the addition of an aldehyde was provided which unexpectedly leads to near theoretical yields of lignin monomers after hydrogenolysis of the extracted product. These yields were almost in an order of magnitude higher than those obtained from lignin using the same extraction and upgrading method in the absence of formaldehyde.

Thus, the subject of the present invention is a method for producing monomers from lignin via depolymerization comprising the steps of
a) providing a lignocellulose-containing composition,
b) heating the composition of step a) under acidic conditions together with an aldehyde, ketone, boronic acid or a compound selected from 2-methoxypropene, dimethyl carbonate and 2,2-dimethoxypropane (to achieve oligomers from lignin)
c) separating the product of step b)
d) converting the product of step c) into the monomers.

Lignocellulose is considered to be the most abundantly available raw material (biomass) on earth. Lignocellulosic biomass can be classified into virgin biomass, waste biomass and energy crops. Virgin lignocellulosic biomass includes all naturally occurring terrestrial plants such as trees, bushes and grass. Waste lignocellulosic biomass is produced as a low value by-product of various industrial sectors, such as agricultural (corn stover, sugarcane bagasse, straw etc.) and forestry (saw mill and paper mill discards).

Lignocellulose comprises hemicellulose, cellulose and lignin. Hemicellulose and cellulose can both be regarded as carbohydrate polymers. The carbohydrate polymers contain five and six carbon sugar monomers and are bound to lignin.

Lignin can be regarded as an aromatic polymer. Said aromatic polymer contains methoxylated phenyl-propane subunits such as guaiacyl and syringyl subunits.

Xylan is a polysaccharide which belongs to the hemicelluloses, wherein the main monomer unit of xylan is D-xylose. Cellulose can be regraded as a polysaccharide, wherein the main monomer unit is D-glucose which is linked via β-1-4 bindings.

In a preferred embodiment of the present invention the lignocellulose-containing composition is lignocellulosic biomass, preferably virgin lignocellulosic biomass, e.g. wood. The lignocellulosic biomass is preferably derived from trees, such as birch, beech, poplar, cedars, Douglas firs, cypresses, firs, junipers, kauri, larches, pines, hemlocks, redwoods, spruces, and yews. Most preferred is hard wood such as birch and/or beech as lignocellulose-containing composition.

In an alternative preferred embodiment of the present invention the lignocellulose-containing composition is derived from energy crops. Energy crops are crops with high yields of lignocellulosic biomass. In addition, energy crops are fast growing such that the lignocellulosic biomass is available already within a short period of time for example after a couple of months. Examples of energy crops include giant reed, big bluestem, Chinese tallow, camelina, duckweed, purging nut, millettia pinnata, switchgrass and elephant grass.

Step a) of the present invention is the provision of a lignocellulose-containing composition.

It is preferred that the lignocellulose-containing composition is solid at a temperature of 23° C. In a preferred embodiment the lignocellulose-containing composition is air dried. For example the lignocellulose-containing composition is air dried for storage to remove excessive water. The air-dried lignocellulose-containing composition preferably comprises less than 50 wt. %, more preferably less than 30 wt. %, in particular from 0 to 20 wt. % of water.

Further, the lignocellulose-containing composition preferably has a lignin content of 10 wt. % to 40 wt. %, preferably 13 wt. % to 35 wt. %, in particular 15 wt. % to 30 wt. % based on the total weight of the lignocellulose-containing composition, wherein lignin is determined as Klason lignin.

For the determination of Klason lignin, the Klason lignin test is applied. In this test wood particles (0.25-0.50 g) were loaded into 50 mL beakers with the addition of 7.5 mL of a 72 wt. % $H_2SO_4$ solution. The mixture was left at room temperature for 2 h and stirred with a glass rod every 10 minutes. Afterwards the slurry was transferred into a round-bottom flask and 290 mL of water were added to reach a $H_2SO_4$ concentration of 3 wt. %. The glass bottle was sealed with a screw cap and sterilized at 120° C. for 1 h in an autoclave. The resultant solution was filtered and the precipitate was washed with water and dried at 105° C. and weighed to determine Klason lignin.

The content of Klason lignin can be determined by the following equation:

$$\text{Content of Klason lignin } [\%] = \frac{KL \times 100}{LCC},$$

wherein
KL is Klason lignin [g]
LCC is lignocellulose-containing composition [g]

Further, step a) preferably includes the provision of the lignocellulose-containing composition in form of particles, such as chips, flakes, pellets, beads, splints, granules, shivers, dust and fragments. For example trees can be cut and sawn to obtain these particles. Further, to obtain a reduced and more homogeneous size of the particles, these can preferably be sieved to pass a 10 to 26 mesh sieve, preferably a 16 to 20 mesh sieve.

In a preferred embodiment step a) involves suspending the lignocellulose-containing composition in an organic solvent.

An organic solvent can be considered as a carbon-based compound which is preferably in a liquid state at 23° C. An organic solvent can comprise one single organic solvent or a mixture of organic solvents.

It is further preferred that the organic solvent has a boiling point of 60° C. to 250° C., preferably at 1013 mbar. Further, the boiling point is not related to a single temperature but can also refer to a temperature interval, for example when a mixture of organic solvents is used. The boiling point preferably is determined according to Pharm. Eur. 6.0, Chapter 2.2.12.

In a preferred embodiment the organic solvent has a water solubility at 25° C. of more than 50 wt. %, preferably more than 70 wt. %, in particular more than 90 wt. %. The upper limit of the water solubility can be 90 wt. % or preferably 100 wt. %. The water solubility can be determined via visual inspection, i.e. the portion of organic solvent to water is determined until precipitation or until a suspension or a phase separation between water and organic solvent appears.

In a preferred embodiment of the invention the second solvent has a log $K_{ow}$ value of −3.0 to 0.8, preferably of −2.5 to 0.7, more preferably of −1.8 to 0.6, in particular of −1.2 to 0.5.

The $K_{ow}$ value (also known as P-value) is a distribution coefficient (partition coefficient) indicating the ratio of concentrations of a compound in the two phases of an octanol/water (hydrophobic/hydrophilic) mixture. The $K_{ow}$ value is determined according to the following formula $$K_{ow} = P = \frac{c_o^{S_i}}{c_w^{S_i}}$$

wherein
$c_o^{S_i}$ is the concentration of the species i of a chemical compound in the octanol phase and
$c_w^{S_i}$ is the concentration of the species i of a chemical compound in the water phase.

The $K_{ow}$ value (P-value) is generally used in form of the decade logarithm as log $K_{ow}$ (log P).

$$\log K_{ow} = \log P = \log \frac{c_o^{S_i}}{c_w^{S_i}}$$

Examples of organic solvent are alcohols with 1 to 6 carbon atoms, such as methanol, ethanol, propanol, isopropanol, butanol and polyethylene glycol, cyclic ethers, such as tetrahydrofuran and dioxane, nitriles, such as acetonitrile, carboxylic acids, such as formic and acetic acid, carboxamides, such as dimethylformamide and dimethylacetamide, lactones, such as γ-valerolactone, lactams, such as N-methyl-2-pyrrolidone and dimethyl sulfoxide. Preferred are alcohols, such as methanol and ethanol, cyclic ethers such as tetrahydrofuran and dioxane and lactones such as γ-valerolactone. Especially preferred are dioxane and tetrahydrofuran, in particular dioxane.

In a preferred embodiment the organic solvent can comprise water. It is preferred that the organic solvent comprises less than 50 volume percent of water, preferably less than 30 volume percent of water, in particular 0 to 10 volume percent of water.

It is preferred that the suspension can contain 3 to 15 ml, preferably 5 to 12 ml, in particular 6 to 10 ml of organic solvent per one gram of the lignocellulose-containing composition.

Step b) includes heating the composition of step a) under acidic conditions together with an aldehyde, ketone, boronic acid or a compound selected from 2-methoxypropene, dimethyl carbonate and 2,2-dimethoxypropane.

Heating the composition of step a) is regarded as applying heat to the composition provided in step a) to raise the temperature of the composition provided in step a) from the starting temperature to a higher end temperature. In a preferred embodiment of the invention the composition of step a) is provided at a temperature of 15° C. to 25° C., which is considered to be the starting temperature. In a preferred embodiment in step b) a temperature, which is considered to be the end temperature of 35 to 140° C., preferably of 40 to 130° C., in particular of 50 to 120° C., can be applied. It is particular preferred that a temperature of 70 to 100° C., especially of about 80° C. is applied.

To achieve the acidic conditions one or more acidic compounds are added to the composition of step a). An acidic compound can be regarded as a chemical compound if, when added into water, it lowers the pH value to less than 7. Examples of acidic compounds are organic carboxylic acids, such acetic acid and mineral acids, wherein the mineral acids are preferred. Mineral acids are regarded as acids which do not contain a carbon atom. Examples of mineral acids are hydrochloric acid, hydrobromic acid, hydroiodic acid, sulfuric acid, phosphoric acid, boric acid and silicic acid. Preferred are hydrochloric acid, sulfuric acid and phosphoric acid, more preferred hydrochloric acid and phosphoric acid, in particular hydrochloric acid.

In a preferred embodiment 1 to 10 mmol, preferably 2 to 9 mmol, in particular 3 to 7 mmol of the acidic compound per gram of the lignocellulose-containing composition can be used to achieve the acidic conditions.

Further, in step b) an aldehyde, a ketone, a boronic acid or a compound selected from 2-methoxypropene, dimethyl carbonate and 2,2-dimethoxypropane is heated together with the lignocellulose-containing composition under acid condition.

Preferably, in step b) an aldehyde or a ketone is heated together with the lignocellulose-containing composition under acid condition.

More preferably, an aldehyde is used.

An aldehyde is an organic compound which can be generally represented by the following structure:

wherein R is hydrogen or an organic residue, e. g. with 1 to 10 carbon atoms.

The term "organic residue" generally refers to a residue known in organic chemistry. Preferably, the skeleton of the organic residue contains predominately carbon atoms, nitrogen atoms and/or oxygen.

The atom of the residue R, which is covalently bonded to the carbon atom with the double bond to the oxygen atom, is a carbon atom.

In a preferred embodiment of the invention R can be an aromatic residue or an aliphatic residue.

An aromatic residue includes at least one ring system predominately containing carbon, nitrogen, sulphur or oxygen atoms, wherein said ring system comprises, according to the Hückel-Rule, a number of 4n+2 (n=0,1,2, . . . ) delocalized electrons in conjugated double bonds, free electron-pairs or unoccupied p-orbitals.

In a preferred embodiment an aromatic residue refers to a residue with an aromatic skeletal structure, wherein the ring atoms of the aromatic skeletal structure are carbon atoms. In an alternatively preferred embodiment the aromatic residue can be substituted with one or more substituents.

Substituents can preferably be selected independently from one or more of the following substituents: alkyl groups with 1 to 4 carbon atoms, halogen, nitro, nitrile, carboxylic group, carboxylic esters and carboxylic amide, methoxy and ethoxy.

Examples for aromatic residues are phenyl, o-tolyl and p-tolyl. Preferred is phenyl, such that the corresponding aldehyde is benzaldehyde.

In a more preferred embodiment R is an aliphatic residue. An aliphatic residue is a non-aromatic hydrocarbon compound which can comprise, apart from carbons and hydrogen atoms, for example also oxygen, sulphur and nitrogen atoms. The aliphatic residue might be substituted or unsubstituted. The same as described above with regard to the aromatic residue can be applied to the substituents.

In a preferred embodiment R can be an unsubstituted, branched or cyclic aliphatic residue with 3 to 6 carbon atoms. Examples are cyclopropyl, isopropyl and tert.-butyl.

It is more preferred that R can be a substituted or unsubstituted, linear aliphatic residue with 1 to 6 carbon atoms, in particular an unsubstituted, linear aliphatic residue with 1 to 6 carbon atoms.

Examples are methyl, ethyl, propyl and butyl, in particular methyl, such that the aldehyde is acetaldehyde.

In an alternative particularly preferred embodiment R is hydrogen, such that the aldehyde is formaldehyde.

A ketone is an organic compound which can be generally represented by the following structure:

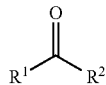

wherein $R^1$ and $R^2$ are independently an organic residue.

With regard to the term "organic residue" the same applies as described above.

In a more preferred embodiment $R^1$ and $R^2$ independently are aliphatic residues. Again with regard to aliphatic residues the same applies as described above.

It is more preferred that $R^1$ and $R^2$ can be independently a substituted or unsubstituted, linear or branched aliphatic residue with 1 to 6 carbon atoms, in particular an unsubstituted, linear aliphatic residue with 1 to 3 carbon atoms.

In a particularly preferred embodiment $R^1$ and $R^2$ both are methyl, such that the ketone is acetone.

In an alternative particularly preferred embodiment $R^1$ is methyl and $R^2$ is ethyl, such that the ketone is butan-2-one.

A boronic acid is a compound which can be generally represented by the following structure:

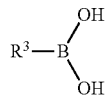

wherein $R^3$ is hydrogen or an organic residue, e. g. with 1 to 10 carbon atoms.

With regard to the term "organic residue" the same applies as described above.

In a more preferred embodiment $R^3$ is an aromatic residue. Again with regard to aromatic residues the same applies as described above.

It is more preferred that $R^3$ can be a substituted or unsubstituted aromatic residue. As far the substituents are concerned the same applies as described above.

It is preferred that $R^3$ is p-tolyl or phenyl, such that the boronic acid is p-tolylboronic acid or phenylboronic acid. In particular, $R^3$ is phenyl, such that the boronic acid is phenylboronic acid.

2-Methoxypropene can be represented by the following structure:

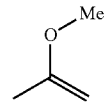

Dimethylcarbonate can be represented by the following structure:

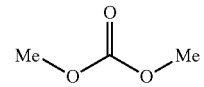

2,2 Dimethoxypropane can be by represented by the following structure:

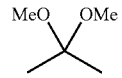

In a preferred embodiment of the invention the lignocellulose-containing composition and the aldehyde, ketone, boronic acid or compound selected from 2-methoxypropene, dimethyl carbonate and 2,2-dimethoxypropane are present in a weight ratio of 25:1 to 1:1, preferably 20:1 to 1.25:1, more preferably 15:1 to 1.5:1, in particular 10:1 to 2:1, wherein the weight of aldehyde, ketone, boronic acid or compound selected from 2-methoxypropene, dimethyl carbonate and 2,2-dimethoxypropane is based on the weight of formaldehyde.

With "based on the weight of formaldehyde" the following is meant. The molecular weight of formaldehyde is 30 g/mol. An aldehyde different from formaldehyde or a ketone has the molecular weight of x g/mol. For example, the molecular weight of acetaldehyde is 44 g/mol and the molecular weight of acetone is 58 g/mol. Thus, to contain the same amount of reactive aldehyde or ketone groups, the aldehyde different from formaldehyde or the ketone has to be present in a weight which is x/30-fold the one of formaldehyde.

For example, the lignocellulose-containing composition and formaldehyde are present in a weight ratio of 25:1, if 25 g lignocellulose-containing composition and 1 g of formaldehyde are provided.

In case that the aldehyde is acetaldehyde, the lignocellulose-containing composition and acetaldehyde having a molecular weight of 44 g/mol are present in a weight ratio of 25:1, if 25 g lignocellulose-containing composition and 1.47 g of aldehyde are provided. 1.47 corresponds to the ratio of the molecular weight of acetaldehyde to the molecular weight of formaldehyde.

Thus, in case the lignocellulose-containing composition and acetaldehyde are present in a weight ratio of 12.5:1 (corresponding to 25:2), 25 g of lignocellulose-containing composition and 2.93 g of acetaldehyde are provided.

In case that the ketone is acetone, the lignocellulose-containing composition and acetone having a molecular weight of 58 g/mol are present in a weight ratio of 25:1, if 25 g lignocellulose-containing composition and 1.93 g of ketone are provided. 1.93 corresponds to the ratio of the molecular weight of acetone to the molecular weight of formaldehyde.

In an alternatively preferred embodiment 1 to 50 mmol, preferably 3 to 35 mmol, more preferably 5 to 25 mmol, in particular 10 to 20 mmol of the aldehyde, ketone, boronic acid or compound selected from 2-methoxypropene, dimethyl carbonate and 2,2-dimethoxypropane per gram of the lignocellulosic-containing composition can be used.

Further, in step (b) the reaction mixture can preferably be subjected to a mechanical movement, such as stirring.

In a preferred embodiment step b) can be carried out between 0.5 and 12 hours, preferably between 0.75 and 10 hours, more preferably between 1 and 8 hours, in particular between 1.5 and 5.5 hours.

By applying step b) the bindings in the lignocellulose-containing composition between the lignin fraction and the cellulose or hemicellulose fractions are cleaved. Further, bindings within the lignin are also cleaved such that "fragments of lignin" are obtained which alternatively can be considered as so-called "oligomers from lignin".

Further, during step b) bindings within the hemicellulose/cellulose fraction can be cleaved such that inter alia so-called "fragments of xylan or glucan" are obtained. In case that in step b) formaldehyde was used the fragments of xylan can comprise diformyl-xylose, which is represented by the following Formula

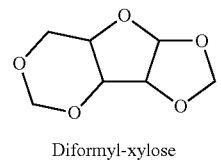 [SMILES: C1OCC2OC3OCOC3C2O1]

Diformyl-xylose

Analytical data with regard to diformyl-xylose is shown in FIG. 6.

In step c) of the method of the present invention the obtained fragments of lignin are separated from the residual mixture of step b).

Step c) can preferably comprise the following sub-steps:
c1) partitioning the fragments of lignin-containing phase and the residue
c2) neutralizing the fragments of lignin-containing phase and removing the solvent
c3) treating the product of step c2) with a solvent and removing the insoluble parts Step c1) can preferably comprise filtering of the mixture. The mixture can be preferably filtered by applying a vacuum at the side of the filtrate. Further, the filter cake can preferably be washed. A suitable washing liquid can for example be acetone or dioxane. Generally, the filter cake can contain cellulose or hemicellulose as well as insoluble substance contained in the lignocellulose-containing composition. The filtrate can be regarded as fragments of lignin-containing phase.

Alternatively preferred step c1) can comprise centrifuging the mixture of step b) and decant the fragments of lignin-containing phase from the residue.

In step c2) the fragments of the lignin-containing phase of step c1), preferably the liquid, fragments of the lignin-containing filtrate, can preferably be neutralized by the addition of an alkaline, inorganic compound. Alkaline, inorganic compounds can for example be hydroxides, carbonates, hydrogen carbonates, phosphates, hydrogen phosphates and sulfates of alkali and earth alkali metals. In a preferred embodiment calcium hydroxide and/or calcium carbonate are used as alkaline inorganic component. More preferred are carbonates of alkali metals, such as sodium carbonate or potassium carbonate, in particular sodium carbonate. After neutralization the solvent can preferably be removed from the resulting mixture, for example at elevated temperature, such as 40 to 60° C., and/or under reduced pressure, such as 20 to 100 mbar.

In step c3) the product of step c2) can be treated with a solvent such as tetrahydrofuran or dioxane, preferably with tetrahydrofuran. Treating the product of step c2) can preferably be carried out under mechanical movement, such as stirring. Further, the treatment with a solvent can preferably be carried out at a temperature of 20° C. to 25° C. After the treatment with a solvent the mixture can be filtered to remove insoluble compounds such that a solution containing the fragments of lignin, is achieved. The fragments of lignin can be obtained by removing the solvent, preferably tetrahydrofuran, from the filtrate. Alternatively, the filtrate containing the fragments of lignin can be further processed without further treatment.

During step c), preferably during sub-steps c1)-c3) the fragments of lignin containing partition preferably further contains the fragments of xylan. For example, the filtrate containing the fragments of lignin or the fragments of lignin obtained when removing the solvent from the filtrate can preferably further comprise the fragments of xylan.

In step d) the fragments of lignin obtained in step c) can be converted into monomers, i.e. into monomers from lignin.

The conversion, which can be regarded as a kind of depolymerisation, can for example be carried out by oxidation and subsequently submitting the oxidized product to acidic condition, such as aqueous formic or acetic acid.

More preferably, the conversion of the fragments of lignin of step c) into the monomers from lignin can be carried out by submitting the fragments of lignin of step c) to a hydrogenolysis.

Generally, hydrogenolysis is a reaction wherein the reaction comprises the cleavage of carbon-carbon or carbon-heteroatom single bonds, wherein this reaction can also be interpreted as "lysis" by hydrogen. The heteroatom is usually oxygen, nitrogen, or sulfur. Usually hydrogenolysis is conducted in the presence of a catalyst and hydrogen.

In a preferred embodiment the conversion of the fragments of lignin obtained in step c), preferably in form of solution, such as the filtrate obtained from step c3), is conducted in the presence of a catalyst.

Suitable catalysts for the hydrogenolysis are for example noble metal catalysts, preferably on carbon. Examples are Ru/C, Pd/C, Pt/C and Rh/C, preferably Ru/C, more preferably 5 wt % Ru/C. It is preferred that the fragments of lignin and the catalyst are present in a weight ratio of 100:1 to 3:1, more preferably of 50:1 to 5:1.

In a preferred embodiment the conversion of the fragments of step c) is conducted in an autoclave, such as a Parr reactor, preferably by the application of a mechanical movement, such as stirring.

Further, in step d) the conversion by hydrogenolysis can be conducted in the presence of hydrogen, preferably in the presence of pressurized hydrogen. For this purpose for example the Parr reactor can be pressurized with 2 to 60 bar, preferably with 7 to 50 bar, more preferably with 10 to 40 bar of hydrogen. Further pressurizing with hydrogen can be exerted up to seven times during the conversion, preferably two or three times.

In a preferred embodiment of the invention step d) can be carried at a temperature of 100° C. to 300° C., preferably 150° C. to 290° C., more preferably 200° C. to 280° C. It is particularly preferred that a temperature of about 250° C. can be applied.

It is further preferred that step d) can be carried out for between 2 and 24 hours, preferably between 3 and 21 hours, more preferably between 4 and 18 hours, in particular between 5 and 16 hours.

In a preferred embodiment the catalyst is removed from the mixture which was submitted to hydrogenolysis reaction, preferably by filtration. Further, the solvent can preferably be removed from the resulting mixture, for example at elevated temperature, such as 40 to 60° C., and/or under reduced pressure, such as 20 to 100 mbar.

In a preferred embodiment the organic solvent used in the method of the present invention can be recycled. This applies for example to the solvent removed in step c2) or to the solvent in which the fragment of lignin are dissolved to be submitted to the hydrogenolysis (step d).

It is further preferred that the monomers from lignin obtained from conversion of the fragments of lignin of step c) can be separated from each other for example by distillation. The monomers can be isolated.

In a preferred embodiment in step (d) fragments of xylan can be obtained (in addition to the monomers from lignin). Preferably, the fragments of xylan contain diformyl-xylose. The fragments of xylan can be separated and, if desired, isolated.

Examples of monomers of lignin which can be obtained by the method of the present invention can be represented by the following formulae (M1 to M24)

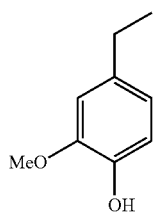
(M1)

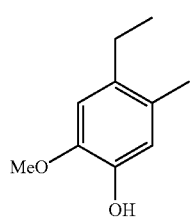
(M2)

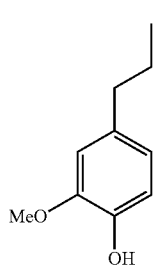
(M3)

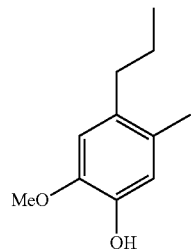
(M4)

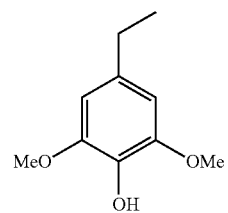
(M5)

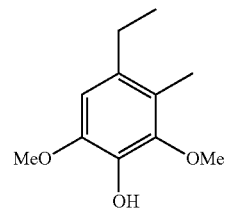
(M6)

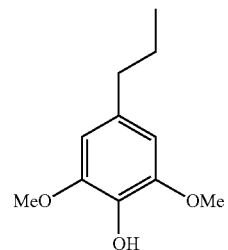
(M7)

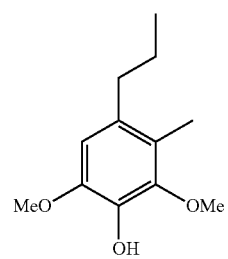
(M8)

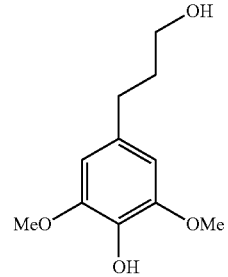
(M9)

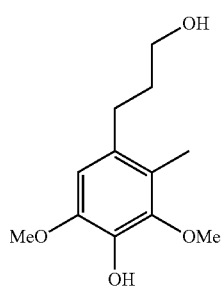 (M10)
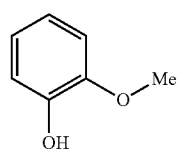 (M11)
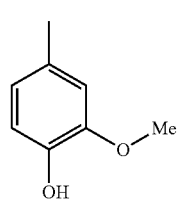 (M12)
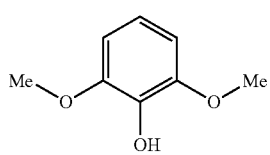 (M13)
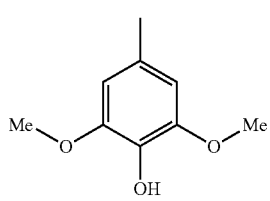 (M14)
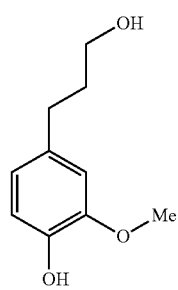 (M15)
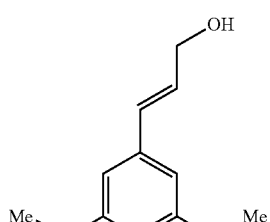 (M16)
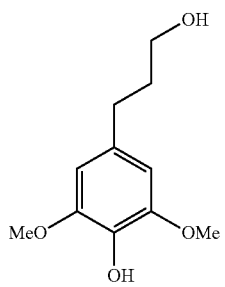 (M17)
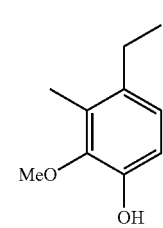 (M18)
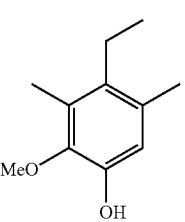 (M19)
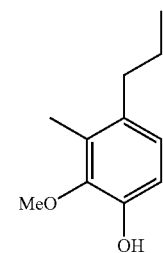 (M20)
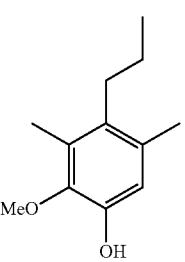 (M21)
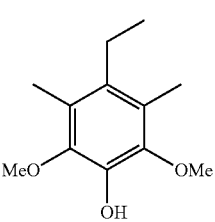 (M22)

(M23)

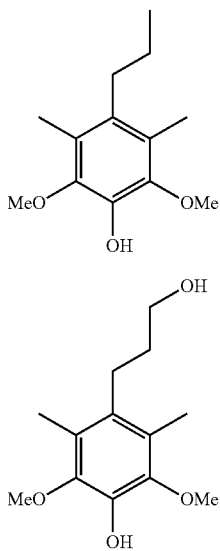

(M24)

wherein
(M1) is 4-ethyl-2-methoxyphenol corresponding to guaiacyl ethane,
(M2) is 4-ethyl-2-methoxy-5-methylphenol corresponding to methylated guaiacyl ethane,
(M3) is 2-methoxy-4-propylphenol corresponding to guaiacyl propane,
(M4) is 2-methoxy-5-methyl-4-propylphenol corresponding to methylated guaiacyl propane
(M5) is 4-ethyl-2,6-dimethoxyphenol corresponding to syringyl ethane,
(M6) is 4-ethyl-2,6-dimethoxy-3-methylphenol corresponding to methylated syringyl ethane,
(M7) is 2,6-dimethoxy-4-propylphenol corresponding to syringyl propane
(M8) is 2,6-dimethoxy-3-methyl-4-propylphenol corresponding to methylated syringyl propane
(M9) is 4-(3-hydroxypropyl)-2,6-dimethoxyphenol corresponding to syringyl propanol
(M10) is 4-(3-hydroxypropyl)-2,6-dimethoxy-3-methylphenol corresponding to methylated syringyl propanol
(M11) is 2-methoxyphenol
(M12) is 2-methoxy-4-methylphenol
(M13) is 2,6-dimethoxyphenol
(M14) is 2,6-dimethoxy-4-methylphenol
(M15) is 4-(3-hydroxypropyl)-2-methoxyphenol
(M16) is (E)-4-(3-hydroxyprop-1-enyl)-2,6-dimethoxyphenol
(M17) is 4-(3-hydroxypropyl)-2,6-dimethoxyphenol corresponding to syringyl propanol (a stereoisomer of M9)
(M18) is 4-ethyl-2-methoxy-3-methylphenol corresponding to an isomer of methylated guaiacyl ethane,
(M19) is 4-ethyl-2-methoxy-3,5-dimethylphenol corresponding to double methylated guaiacyl ethane,
(M20) is 4-propyl-2-methoxy-3-methylphenol corresponding to an isomer of methylated guaiacyl propane,
(M21) is 4-propyl-2-methoxy-3,5-dimethylphenol corresponding to double methylated guaiacyl propane,
(M22) is 4-ethyl-2,6-dimethoxy-3,5-dimethylphenol corresponding to double methylated syringyl ethane,
(M23) is 4-propyl-2,6-dimethoxy-3,5-dimethylphenol corresponding to double methylated syringyl propane,
(M24) is 4-(3-hydroxypropyl)-2,6-dimethoxy-3,5-dimethylphenol corresponding to double methylated syringyl propanol During the step of converting the fragments of lignin into monomers, preferably by hydrogenolysis, the fragments of xylan can remain unchanged. In a preferred embodiment, the fragments from xylan can be separated from the monomers of lignin, for example by distillation or by crystallisation.

In an embodiment of the invention step the fragments of xylan can be further converted to xylose. This conversion can preferably comprise the reaction of the fragments of xylan in water under acidic conditions. As far as the acidic conditions are concerned the same applies as mentioned above. Preferred acids are hydrochloric acid and sulfuric acid in particular sulfuric acid.

In an embodiment the conversion of the fragments of xylan is conducted in 1 to 7 wt %, preferably 2 to 5 wt %, more preferably about 3 wt % sulfuric acid in water.

In an embodiment the conversion of the fragments of xylan conducted in an autoclave, such as a Parr reactor, preferably by the application of a mechanical movement, such as stirring.

In an embodiment of the invention the conversion of the fragments of xylan can be carried at a temperature from 60° C. to 200° C., preferably from 80° C. to 180° C., more preferably from 100° C. to 150° C. It is particularly preferred that a temperature of about 120° C. can be applied.

It is further preferred that the conversion of the fragments of xylan can be carried out for between 15 and 240 minutes, preferably between 30 and 180 minutes, more preferably between 45 and 120 minutes, in particular about 60 minutes.

Thus, in a further aspect of the invention is related to the production of fragments of xylan. A preferred fragment of xylan is diformyl-xylose.

Thus, a further subject of the invention is a method for producing fragments of xylan via depolymerization comprising the steps of
a) providing a lignocellulose-containing composition,
b) heating the composition of step a) under acidic conditions together with an aldehyde, ketone, boronic acid or a compound selected from 2-methoxypropene, dimethyl carbonate and 2,2-dimethoxypropane, preferably an aldehyde, in particular formaldehyde,
c') separating fragments of xylan from the mixture of step b).

As far as the reaction condition and components in step a) and b) are concerned the same as described above with regard to step a) and b) applies.

It is preferred that in step b) an aldehyde or a ketone is heated together with the composition of step a) under acid condition.

In step c') the fragments of xylan are separated from the residual mixture of step b).

Step c') can preferably comprise the following sub-steps:
c1) partitioning the fragments of xylan-containing phase and the residue
c2) neutralizing the fragments of xylan-containing phase and removing the solvent
c3) treating the product of step c2) with a solvent and removing the insoluble parts
c'4) submitting the mixture from step c3) to a hydrogenolysis and separating the fragments xylan thereafter As far as the reaction condition and components in sub-steps c1) to c3) are concerned the same as described above with regard to sub-steps c1) to c3) applies.

In step c4) the mixture obtained in step c3) can be preferably submitted to a hydrogenolysis As far as the hydrogenolysis of the mixture obtained in step c3) is concerned the same conditions and component as described above can be used. The fragments of xylan can be separated from the mixture obtained by the hydrogenolysis for example by distillation or by crystallisation.

In a preferred embodiment, in case that the aldehyde used in step b) is formaldehyde the fragments of xylan can be distilled at an elevated temperature and/or under reduces pressure, preferably at a temperature of about 120° C. and a pressure of about 0.1 mbar. The resulting fragment of xylan is diformyl-xylose. Diformyl-xylose can be identified by different spectra derived form the corresponding determination methods as shown in FIG. 6.

Optionally, the fragments of xylan can be further converted to xylose. As far as the conversion of the fragments of xylan to xylose is concerned the same conditions and components as described above can be used.

A further subject of the present invention is the use of formaldehyde in the depolymerization of a lignocellulose-containing composition. In a preferred embodiment formaldehyde is used for producing monomers from lignin by depolymerizing a lignocellulosic biomass.

In a further preferred embodiment formaldehyde, acetaldehyde or propionaldehyde are used for producing fragments of xylan, in particular diformyl-xylose or other ketone-xylose or aldehyde-xylose, ketone-xylan or aldehyde-xylan adducts, by depolymerizing a lignocellulosic biomass.

In a further preferred embodiment formaldehyde, acetaldehyde or propionaldehyde are used for producing fragments of glucan, in particular glucose, gluco-oligomers, ketone-glucose or aldehyde-glucose, ketone-glucan or aldehyde-glucan adducts, by depolymerizing a lignocellulosic biomass.

In a preferred embodiment monomers from lignin (lignin-derived fragments) are used for the production of resins including phenyl formaldehyde resin substitutes and thermosets.

In a preferred embodiment monomers from lignin (lignin-derived fragments) are used for the production of transportation fuels.

In a preferred embodiment monomers from lignin (lignin-derived fragments) are used for the production of monomers for polymer production including styrenes, methacrylates and polyesters.

As far as the compounds and conditions for the depolymerization of the lignocellulose-containing composition are concerned they correspond to the ones as described in the present method.

The invention will now be illustrated with reference to the following examples.

EXAMPLES

I. Materials

All commercial chemicals were analytical reagents and were used without further purification. 5% Ru on carbon (Ru/C), guaiacol (2-methoxyphenol, 98%), 4-ethyl-guaiacol (>97%), 4-propylguaiacol (>99%), syringol (2, 6-dimethoxyphenol, 99%) and propylbenzene (98%) were purchased from Sigma Aldrich. Methanol (>99%), tetrahydrofuran (THF, >99%) and dichloromethane (>99%) were purchased from ABCR. 4-Propanolguaiacol (3-(4-hydroxy-3-methoxyphenyl)-1-propanol, >98%), 1,4-dioxane (98%) were purchased from TCI chemicals. Beech wood (*Fagus sylvatica*) was harvested in Zollikofen (Switzerland) in October 2014 and air dried for storage. Prior to experiments the beech chips were reduced in size to pass through a 18 mesh sieve.

II. Analytical Methods (1) Composition Analysis of Biomass

The composition analysis of biomass and substrate after lignin extraction followed the TAPPI method. The, wood particles (0.25-0.50 g) were loaded into 50 mL beakers with the addition of 7.5 mL of a 72 wt. % $H_2SO_4$ solution. The mixture was left at room temperature for 2 h and stirred with a glass rod every 10 minutes. Afterwards the slurry was transferred into a round-bottom flask and 290 mL of water were added to reach a $H_2SO_4$ concentration of 3 wt. %. The glass bottle was sealed with a screw cap and sterilized at 120° C. for 1 h in an autoclave. The resultant solution was filtered and the filtrate was used for sugar analysis on an HPLC and the precipitate was washed with water and dried at 105° C. and weighed to determine Klason lignin.

For the analysis of pretreatment liquor, the slurry after lignin extraction was filtered and washed with 30 mL water and analyzed by high performance liquid chromatography (HPLC). To hydrolyze possible oligomers or acetalized sugars into monomeric sugars, 20 μL concentrated sulfuric acid was added to 1 mL of the filtrate and heated to 120° C. for 1 h in an autoclave. The resulting mixture was analyzed by HPLC.

Analysis of the sugars was conducted using an Agilent Infinity 1260 HPLC system equipped with a Refractive Index Detector and a Bio-Rad Aminex HPX-87P column at 80° C. using water as the mobile phase and a flow rate of 0.6 ml/min.

Analysis of Furfural and HMF was conducted using an Agilent Infinity 1260 HPLC equipped with UV-Vis Detector and a Bio-Rad Aminex HPX-87H column at 80° C. using 5 mM $H_2SO_4$ in water as the mobile phase and a flow rate of 0.6 ml/min.

The composition analysis of beech wood particles resulted in the following:

| | Compound | | | | | |
|---|---|---|---|---|---|---|
| | glucose | Xylose | arabinose | galactose | mannose | Klason lignin |
| Content | 34% | 14% | 2% | 2% | 2% | 22% |

(2) Lignin Monomer Analysis

To analyze lignin monomers after hydrogenolysis, 1 mL of the resultant solution was directly sampled for analysis without any further treatment other than the addition of 100 μL of prepared internal standard (8 mg decane in 5 mL dioxane). The solution (~1.1 mL) was analyzed with a GC (Agilent 7890B series) equipped with an HP5-column and a flame ionization detector (FID). The injection temperature was 573 K. The column temperature program was: 313 K (3 min), 30 K/min to 373 K, 40 K/min to 573 K and 573 K (5 min). The detection temperature was 573 K. Sensitivity factors of the products were obtained by using estimates based on the effective carbon number due to lack of commercial standards. The monomer yield was calculated as followed:

$$n_{decane} = \frac{W_{decane\ in\ sample}}{MW_{decane}} \quad (S1)$$

$$n_{monomer} = \frac{A_{monomer\ in\ sample}}{A_{decane\ in\ sample}} \times n_{decane} \times \frac{ECN_{decane}}{ECN_{monomer}} \quad (S2)$$

$$W_{monomer} = n_{monomer} \times MW_{monomer} \quad (S3)$$

$$Y_{monomer} = \frac{W_{monomer} \times V}{W_{extracted\ lignin}} \times 100\% \quad (S4)$$

In the equations,
$W_{decane\ in\ sample}$ (mg): the weight of decane as internal standard in each analyzed sample;
$MW_{decane}$ (mg mmol$^{-1}$): the molecular weight of decane (142 mg mmol$^{-1}$);
$n_{decane}$ (mmol): the molar amount of decane in each analyzed sample;
$n_{monomer}$ (mmol): the molar amount of monomer in each analyzed sample;
$A_{monomer\ in\ sample}$: the peak area of monomer in GC-FID chromatogram;
$A_{decane\ in\ sample}$: the peak area of decane in the GC-FID chromatogram;
$ECN_{decane}$: the effective carbon number (10) of a decane molecule;
$ECN_{monomer}$: the effective carbon number of the lignin monomer molecule;
$W_{monomer}$ (mg): the molecular weight of dehydrated monomer units (guaiacyl glycerol (196 mg mmol$^{-1}$) or dehydrated syringyl glycerol (226 mg mmol$^{-1}$)) depending on the analyzed monomer;
$Y_{monomer}$: the yield of monomer based on the weight of extracted lignin;
$W_{extracted\ lignin}$ (mg): the weight of extracted lignin;
V (mL): the total volume of the sample, 1 mL of which was used for GC analysis.

Identification of monomer peaks in the GC-FID chromatograms was performed initially by GC-MS using an Agilent 7890B series GC equipped with a HP5-MS capillary column and an Agilent 5977A series Mass Spectroscopy detector. The peaks in the GC-MS chromatogram appear in the same orders as those in GC-FID chromatogram due to the use of a similar capillary column. The following operating conditions were used: injection temperature at 523 K, a column temperature program of 323 K (1 min), 15 K/min to 573 K and 573 K (7 min) and a detection temperature of 563 K.

(3) NMR Analysis of Lignin

A dried sample was dissolved in 600-1000 µL D-chloroform and transferred into NMR sample tubes. NMR spectra were acquired on a Bruker Avance III 400 MHz spectrometer. The chloroform solvent peak was used as an internal reference ($\delta_C$, 77.2 ppm; $\delta_H$, 7.24 ppm).

(4) Gel Permeation Chromatography (GPC) Analysis

A dried sample was dissolved in 600-1000 THF and GPC analysis was conducted using an Agilent Infinity 1260 HPLC equipped with a Refractive Index Detector and an Agilent PLgel MIXED C column at 40° C. using THF as the mobile phase and a flow rate of 1 ml/min.

III. Monomer Identification and Quantification

Validation of the Effective Carbon Number Method

The effective carbon number (ECN) rule has been widely used to quantify carbon-containing products based on its response in GC-FID when an authentic standard compound is not available or available only in limited quantities. ECN is the sum of the contributions made by the individual carbon atoms modified by their functional group contributions. Due to the structural differences of different molecules, the accuracy of this rule can vary. In order to verify the accuracy of this rule applied to lignin monomer quantification, the effective carbon numbers of six different lignin model compounds were measured based on their known quantity and their GC response compared to that of decane. The ECN calculated based on FID response using decane as an internal standard was compared to the theoretical ECN based on this empirical rule. For this purpose it is referred to following FIG. 1. Based on the empirical rule, carbons connected only to hydrogen and carbon atoms add 1 unit to the ECN, carbon atoms in a methoxy group (ether) are predicted to not add to the FID response, carbons connected to primary hydroxyl group add 0.5-0.6 units to the ECN and carbon connected to phenolic hydroxyl typically add 0.5 units to the ECN. The only inconsistency we found is that carbon connected to phenolic hydroxyl in lignin monomers did not contribute to the ECN. The contributions of carbon in lignin monomers to ECN (corresponding to increments to calculate the ECN) are summarized in the table below:

| Atom/group | ECN contribution |
| --- | --- |
| Carbon-aliphatic | 1 |
| Carbon-aromatic | 1 |
| Oxygen-primary alcohol | −0.5 |
| Oxygen-phenol | −1 |

Based on this adjusted ECN rule, the ECNs calculated experimentally matched those based on the ECN rule with errors below 1% for all compounds. This demonstrated the high accuracy of using decane as an internal standard and using the factor $ECN_{monomer}/ECN_{decane}$ (Equation S2) to quantify lignin monomers. Based on these results, we followed the empirical rule with the modified phenolic carbon connected to the hydroxyl group contribution of 0 for calculating the ECN of biomass-derived lignin monomers. All effective carbon numbers of lignin monomers ($ECN_{monomers}$) used for quantification are listed in the following Table:

TABLE

Effective carbon number for lignin monomers

| Lignin monomer structure | Effective carbon number used based on adjusted ECN rule ($ECN_{monomer}$) |
| --- | --- |
| 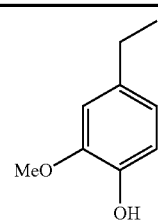 | 7 |

TABLE-continued

Effective carbon number for lignin monomers

| Lignin monomer structure | Effective carbon number used based on adjusted ECN rule ($ECN_{monomer}$) |
|---|---|
| 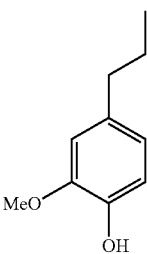 | 8 |
| 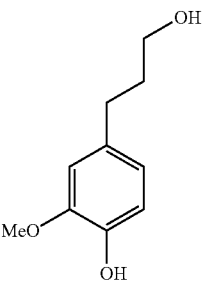 [SMILES: COc1cc(CCCO)ccc1O] | 7.5 |
| 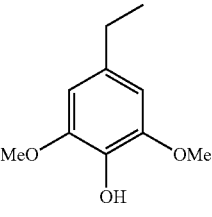 | 7 |
| 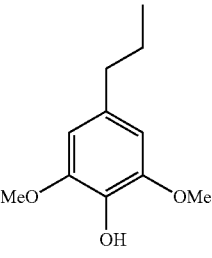 | 8 |
| 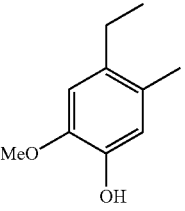 | 8 |
| 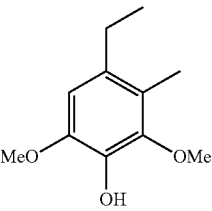 | 8 |

TABLE-continued

Effective carbon number for lignin monomers

| Lignin monomer structure | Effective carbon number used based on adjusted ECN rule ($ECN_{monomer}$) |
|---|---|
| 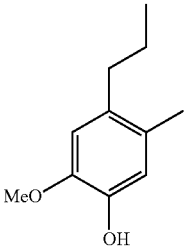 | 9 |
| 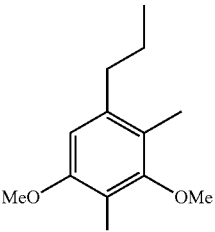 | 9 |
| 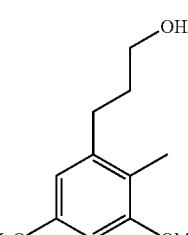 | 8.5 |
| 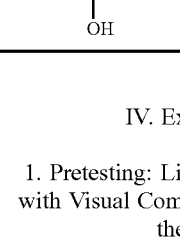 | |

IV. Experimental Procedure

1. Pretesting: Lignin Extraction (Steps a) and b) with Visual Comparison Example 1 According to the Present Invention In a 50 mL glass vial, 1 g of air-dried beech wood particles, 9 mL of dioxane, 420 μL HCl-solution (36.5-37% in water) (180-185 mg HCl and 315 μL water) and 1 mL formaldehyde solution (36.5% in water) (400 mg FA and 690 μL water) were added. The reaction was conducted in an oil bath set at 80° C. for five hours and stirred by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water) and further diluted with water to precipitate the "fragments of lignin".

Reference Example 1 (without Addition of Formaldehyde)

In a 50 mL glass vial, 1 g of air-dried beech wood particles, 9 mL of dioxane, 420 μL HCl-solution (36.5-37% in water) (180-185 mg HCl and 315 μL water) and 690 μL water were added. The reaction was conducted in an oil bath set at 80° C. for five hours and stirred by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water) and further diluted with water to precipitate the extracted lignin. Pictures were taken directly after the addition of water and 15 hours after the addition of water.

As can be seen from FIG. 2, the color of the "fragments of lignin" obtained by Example 1 according to the present invention is light, suggesting a limited condensation, while the darker color of the "fragments of lignin" obtained by Reference Example 1 indicates an undesirable, severe condensation.

2. Producing Monomers (Steps a)-d))

Examples 2.1 to 2.6 According to the Present Invention (Steps a)-c))

In a 50 mL glass vial, 1 g of air-dried beech wood particles, 9 mL of dioxane, 420 µL HCl-solution (36.5-37% in water) (180-185 mg HCl and 315 µL water) and 1 mL formaldehyde solution (36.5% in water) (400 mg FA and 690 µL water) were added. The reaction was conducted in an oil bath set at the corresponding specified temperature and stirred for corresponding specified hours by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water). The solvent was removed in a rotatory evaporator set at 60° C. The dried residue was dissolved in 25 mL THF to extract lignin, leaving the salt and carbohydrates as precipitates.

Examples 2.1 to 2.6 According to the Present Invention (Step d); Hydrogenolysis)

20 mL of the obtained lignin-THF solution along with 100 mg of catalyst (5 wt % Ru/C) was added to a 50 mL high-pressure Parr reactor. The reactor was stirred with a magnetic stir bar and heated with high-temperature heating tape (Omega) connected to a variable power supply controlled by a PID temperature controller (Omega) with a K-type thermocouple that measured the reaction temperature through a thermowell. Once closed, the reactor was purged 3 times and then pressurized with 40 bar of hydrogen. The reactor was heated to the corresponding specified temperature and then held at that temperature for a corresponding specified residence time. After reaction, the reactor was cooled with an external flow of compressed air at room temperature. A sample of the resulting liquid was taken for GC analysis.

Example 2.7

The conditions for the lignin extraction as described in Examples 2.1 to 2.6 are correspondingly applied as described above. The slurry after reaction was filtered and washed with 10 mL dioxane. The filtrate was then neutralized with a sodium bicarbonate solution (~420 mg in 5 mL water). Dioxane was added to the neutralized solution to reach 25 mL and centrifuged to remove any precipitated salts.

20 mL of the resulting lignin-dioxane solution along with 100 mg of catalyst (5 wt % Ru/C) were added to a 50 mL high-pressure Parr reactor and the remaining procedure was preformed as described above, wherein the reactor was heated to the corresponding specified temperature and then held at that temperature for the corresponding specified residence time.

Example 2.8

The same conditions as described in Examples 2.1 to 2.6 (steps a)-d)) are applied, wherein after removing the solvent the dried residue was dissolved in 25 mL methanol before being submitted to the hydrogenolysis.

Example 2.9

The same conditions as described in Examples 2.1 to 2.6 (steps a)-d)) are applied, wherein in the lignin extraction only 1/10 of the formaldehyde loading is used.

Example 2.10

The same conditions as described in Examples 2.7 are applied, wherein in the γ-valerolactone (GVL) was used for steps a)-c) as well as for step d).

FIG. 3a shows a GC chromatogram and FIG. 3b a mass spectrum of monomers from lignin (aromatic compounds) obtained by the method of the present invention. FIG. 4 shows data with regard to the NMR-characterization of the monomers from lignin. With regard to all of this data it can be seen that the method of the present invention provides ten different aromatic compounds which were identified.

Reference Example 2.1 (Step a)-c) without Adding of Formaldehyde)

In a 50 mL glass vial, 1 g of air-dried beech wood particles, 9 mL of dioxane, 420 µL HCl-solution (36.5-37% in water) (180-185 mg HCl and 315 µL water) and 690 µL water were added. The reaction was conducted in an oil bath set at 80° C. for five hours and stirred by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water). The solvent was removed in a rotatory evaporator set at 60° C. The dried residue was dissolved in 25 mL THF to extract lignin, leaving the salt and carbohydrates as precipitates.

Step d) (Hydrogenolysis)

20 mL of the obtained lignin-THF solution along with 100 mg of catalyst (5 wt % Ru/C) were added to a 50 mL high-pressure Parr reactor and the remaining procedure was preformed as in Examples 2.1 to 2.9, wherein the reactor was heated to 200° C. and then held at that temperature for 6 hours.

Reference Example 2.2 (Only Step d))

1 g of wood powder was mixed with 20 mL of tetrahydrofuran and 200 mg of the 5 wt % Ru/C catalyst. The slurry was added to a 50 mL high-pressure Parr reactor and the remaining procedure was preformed as in Examples 2.1 to 2.9, wherein the reactor was heated to 250° C. and then held at that temperature for 15 hours.

Reference Example 2.3

The procedure is carried out as in Reference Example 2.2, wherein methanol instead of tetrahydrofuran is used.

The amount of extracted lignin was determined by subtracting the amount of Klason lignin in the extracted residue from the amount of Klason lignin in untreated wood.

Table 1 shows the specific reaction conditions with regard to extraction and hydrogenolysis and the yields of monomers from lignin (aromatic compounds) obtained by the corresponding specific reaction conditions. From said Table it can be seen that every one of present Examples 2.1 to 2.10 shows a significantly higher monomer yield based on extracted lignin than Reference Example 2.1 wherein the extraction step is conducted in the absence of formaldehyde.

E3.2 was carried out as E3.1, wherein the formaldehyde solution was substituted by a molar equivalent of acetaldehyde in addition with 690 µL water.

E3.3 was carried out as E3.1, wherein the formaldehyde solution was substituted by a molar equivalent of propionaldehyde in addition with 690 µL water.

E3.4 was carried out as E3.1, wherein the formaldehyde solution was substituted by a molar equivalent of benzaldehyde in addition with 690 µL water.

TABLE 1

Yields of monomers from in different reaction conditions. M1-M10 correspond to the following monomers. M1: guaiacylethane, M2: methylated guaiacylethane, M3: guaiacylpropane, M4: methylated guaiacylpropane, M5: syringylethane, M6: methylated syringylethane, M7: syringylpropane, M8: methylated syringylpropane, M9: syringylpropanol, M10: methylated syringylpropanol. Further, from Reference Examples 2.2 and 2.3 it can be seen that direct hydrogenolysis of the sample leads to a high yield of monomers from lignin. However, the yield is not the only decisive factor. The direct hydrogenolysis bears the disadvantages as described above. In addition, with reference to FIG. 5, only a small variety of aromatic compounds is obtained under direct hydrogenolysis applied in both Reference Examples 2.2 and 2.3. The present method, on the contrary, provides a larger diversity of aromatic compounds.

| Example | Steps a)-c) | Step d) | Extracted lignin yield (%) | M1 (%) | M2 (%) | M3 (%) | M4 (%) | M5 (%) | M6 (%) | M7 (%) | M8 (%) | M9 (%) | M10 (%) | Monomer yield based on extracted lignin (%) | Monomer yield based on native lignin (%) |
|---|---|---|---|---|---|---|---|---|---|---|---|---|---|---|---|
| 2.1 | 80° C., 5 h | 200° C., 6 h | 80 | 0.76 | 0 | 8.36 | 2.71 | 2.44 | 1.28 | 15.88 | 11.26 | 6.77 | 4.30 | 53.77 | 42.82 |
| 2.2 | 80° C., 1.5 h | 250° C., 15 h | 50 | 4.82 | 0.48 | 11.05 | 1.99 | 14.85 | 3.75 | 23.00 | 4.70 | 0 | 0.52 | 65.17 | 32.44 |
| 2.3 | 80° C., 5 h | 250° C., 15 h | 80 | 0.36 | 0.77 | 7.47 | 2.72 | 11.59 | 6.74 | 14.48 | 8.38 | 0 | 0.48 | 52.98 | 42.19 |
| 2.4 | 100° C., 2 h | 250° C., 15 h | 73 | 3.43 | 0.60 | 9.29 | 2.53 | 11.64 | 5.26 | 18.72 | 7.89 | 0 | 0.53 | 59.89 | 43.52 |
| 2.5 | 120° C., 1 h | 250° C., 15 h | 77 | 2.71 | 0.39 | 5.24 | 2.03 | 7.84 | 6.21 | 10.47 | 8.21 | 0.99 | 1.38 | 45.46 | 34.84 |
| 2.6 | 100° C., 3 h | 250° C., 15 h | 79 | 3.17 | 0.69 | 5.00 | 2.40 | 8.88 | 7.56 | 9.51 | 8.14 | 0.57 | 0.92 | 46.85 | 36.84 |
| 2.7 | 100° C., 2 h | 250° C., 15 h | 73 | 6.88 | 0.78 | 6.50 | 1.80 | 20.12 | 7.49 | 12.30 | 4.97 | 0 | 0.34 | 61.72 | 44.85 |
| 2.8 | 80° C., 5 h | 230° C., 15 h | 80 | 1.22 | 0 | 4.76 | 1.51 | 2.73 | 1.84 | 9.38 | 9.07 | 9.66 | 5.61 | 45.77 | 36.45 |
| 2.9 | 80° C., 5 h | 250° C., 15 h | 78 | 5.21 | 0 | 3.51 | 1.02 | 18.46 | 0.18 | 8.64 | 0.90 | 0.32 | 0.39 | 38.62 | 29.99 |
| 2.10 | 100° C., 2 h | 250° C., 15 h | 65 | 0.3 | 0 | 6.5 | 2.7 | 0.5 | 0.5 | 13.6 | 8.9 | 5.1 | 3.2 | 63.4 | 41.30 |
| R.E 2.1 | 80° C., 5 h | 200° C., 6 h | 78 | 0.67 | 0 | 0.81 | 0 | 2.54 | 0 | 2.23 | 0 | 2.45 | 0 | 8.70 | 6.75 |
| R.E 2.2 | / | 250° C., 15 h | / | 0.51 | 0 | 9.60 | 0 | 1.24 | 0 | 23.05 | 0 | 11.66 | 0 | / | 45.86 |
| R.E 2.3 | / | 250° C., 15 h | / | 7.79 | 0 | 1.78 | 0 | 21.62 | 0 | 3.22 | 0 | 0 | 0 | / | 34.25 |

Example 3

Examples E3.1 to E3.10; Steps a) to c) According to the Invention

E3.1 In a 50 mL glass vial, 1 g of air-dried birch wood particles, 9 mL of dioxane, 420 µL HCl-solution (36.5-37% in water) (180-185 mg HCl and 315 µL water) and 1 mL formaldehyde solution (36.5% in water) (400 mg FA and 690 µL water) were added. The reaction was conducted in an oil bath set at 90° C. for 3.5 hours and stirred by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water). The solvent was removed in a rotary evaporator set at 60° C. The dried residue was dissolved in 25 mL THF to extract the lignin, leaving the salt and carbohydrates as precipitates.

E3.5 was carried out as E3.1, wherein the formaldehyde solution was substituted by a molar equivalent of acetone in addition with 690 µL water.

E3.6 was carried out as E3.1, wherein the formaldehyde solution was substituted by a molar equivalent of 2-butanone in addition with 690 µL water.

E3.7 was carried out as E3.1, wherein the formaldehyde solution was substituted by a molar equivalent of phenylboronic acid in addition with 690 µL water.

E3.8 was carried out as E3.1, wherein the formaldehyde solution was substituted by a molar equivalent of 2-methoxypropene in addition with 690 µL water.

E3.9 was carried out as E3.1, wherein the formaldehyde solution was substituted by a molar equivalent of dimethyl carbonate in addition with 690 µL water.

E3.10 was carried out as E3.1, wherein the formaldehyde solution was substituted by a molar equivalent of 2,2-dimethoxypropane in addition with 690 µL water.

Control Examples CE3.1 and CE3.2

In a 50 mL glass vial, 1 g of air-dried birch wood particles, 9 mL of dioxane, 420 µL HCl-solution (36.5-37% in water) (180-185 mg HCl and 315 µL water) and 690 µL water were added. The reaction was conducted in an oil bath set at 90° C. for 3.5 hours and stirred by a stir bar at a stirring speed of 300 rpm. After the reaction, the slurry was filtered and washed with acetone until the filtrate was colorless. The filtrate was then neutralized by addition of a sodium bicarbonate solution (~420 mg in 5 mL water). The solvent was removed in a rotatory evaporator set at 60° C. The dried residue was dissolved in 25 mL THF to extract lignin, leaving the salt and carbohydrates as precipitates.

Step d) Hydrogenolysis 20 mL of every of the obtained lignin-THF solutions from E3.1 to E3.10 as well as CE3.1 and CE3.2 as described above and each along with 100 mg of catalyst (5 wt % Ru/C) was added to a 50 mL high-pressure Parr reactor, respectively. The reactor was stirred with a magnetic stir bar and heated with high-temperature heating tape (Omega) connected to a variable power supply controlled by a PID temperature controller (Omega) with a K-type thermocouple that measured the reaction temperature through a thermowell. Once closed, the reactor was purged 3 times and then pressurized with 40 bar of hydrogen. The reactor was heated to 250° and then held at that temperature for 15 hours. After reaction, the reactor was cooled with an external flow of compressed air at room temperature. A sample of the resulting liquid was taken for GC analysis.

Table 2 shows the specific Examples with regard to and the yields of monomers from lignin (aromatic compounds) obtained by the addition of the specific aldehydes, ketones, boronic acids and compounds selected from 2-methoxypropene, dimethyl carbonate and 2,2-dimethoxypropane.

TABLE 2

Yields of monomers from lignin

| Example | M1 (%) | M2 (%) | M3 (%) | M4 (%) | M5 (%) | M6 (%) | M7 (%) | M8 (%) | M9 (%) | M10 (%) | M11 (%) | M12 (%) | M13 (%) | M14 (%) | M15 (%) | M16 (%) | M17 (%) | Yield M1-M17 [wt.(%)] |
|---|---|---|---|---|---|---|---|---|---|---|---|---|---|---|---|---|---|---|
| 3.1 | 3.35 | 0.50 | 2.91 | 1.07 | 16.29 | 6.79 | 6.66 | 5.68 | 0.36 | 0.53 | 0.16 | 0.27 | 0 | 1.36 | 0.47 | 0 | 0.23 | 46.55 |
| 3.2 | 4.93 | 0 | 1.79 | 0 | 22.83 | 0 | 4.22 | 0 | 0 | 0 | 0.24 | 0.58 | 0 | 2.01 | 2.13 | 0 | 0 | 38.737 |
| 3.3 | 5.80 | 0 | 0.89 | 0 | 27.64 | 0 | 3.07 | 0 | 0 | 0 | 0 | 0.95 | 0 | 3.29 | 0.91 | 0.35 | 0.19 | 43.10 |
| 3.4 | 1.35 | 0 | 1.23 | 0 | 6.20 | 0 | 4.81 | 0.30 | 0.32 | 0 | 0.87 | 0.70 | 3.11 | 2.68 | 2.45 | 0.79 | 2.63 | 27.45 |
| 3.5 | 1.48 | 0 | 0.62 | 0 | 7.63 | 0 | 1.64 | 0 | 0.37 | 0 | 0.18 | 1.40 | 0.92 | 5.26 | 0.50 | 0.32 | 1.48 | 21.80 |
| 3.6 | 1.52 | 0 | 0.87 | 0 | 7.24 | 0 | 1.98 | 0 | 0.51 | 0 | 0.67 | 1.54 | 1.11 | 5.98 | 1.12 | 0.51 | 3.89 | 26.96 |
| 3.7 | 3.08 | 0 | 1.33 | 0 | 15.32 | 0 | 4.86 | 0 | 0 | 0 | 0.17 | 0.27 | 0.57 | 0.97 | 0 | 0 | 0 | 26.56 |
| 3.8 | 1.81 | 0 | 0.40 | 0 | 7.21 | 0 | 1.26 | 0 | 0 | 0 | 0.21 | 1.31 | 0.96 | 4.73 | 2.88 | 0.13 | 026 | 21.15 |
| 3.9 | 0.54 | 0 | 1.19 | 0 | 2.31 | 0 | 4.09 | 0.81 | 1.94 | 0 | 0.79 | 0.53 | 2.36 | 1.76 | 1.56 | 0.19 | 2.96 | 21.03 |
| 3.10 | 1.86 | 0 | 0.46 | 0 | 9.63 | 0 | 1.05 | 0 | 0 | 0 | 1.06 | 1.03 | 0.65 | 3.64 | 0 | 0 | 0 | 19.37 |
| CE3.1 | 1.14 | 0.84 | 0.42 | 0 | 5.49 | 0.22 | 1.48 | 0 | 0.13 | 0 | 0.21 | 0.92 | 0 | 4.31 | 0.37 | 0.14 | 1.01 | 16.67 |
| C.E3.2 | 1.21 | 0 | 0.40 | 0 | 5.47 | 0 | 1.41 | 0 | 0.25 | 0 | 0.17 | 0.84 | 0 | 3.92 | 0.30 | 0.150 | 1.17 | 15.30 |

The yields are calculated based on the amount of Klason lignin in 1 g birch (18% Klason lignin).

As can be seen from Table 2 all Examples in which aldehydes (E3.1 to E3.4), ketones (E3.5 and E3.6), boronic acid (E3.7) and compounds selected from 2-metoxypropene, dimethyl carbonate an 2,2-dimethoxypropane (E3.8 to E3.10) were used provide a statistically significantly enhanced total yield of monomers from lignin compared to the control Examples (CE3.1 and CE3.2).

The invention claimed is:

1. A method for producing fragments from lignin via depolymerization comprising the steps of:
   a) providing a lignocellulose-containing composition,
   b) heating the composition of step a) under acidic conditions together with an aldehyde, boronic acid, or a compound selected from 2-methoxypropene, dimethyl carbonate, and 2,2-dimethoxypropane to form a mixture; and
   c) separating fragments of lignin from the mixture of step b),
   wherein step c) comprises the sub-steps:
      c1) partitioning the mixture to form a fragments of lignin-containing phase and a residue;
      c2) neutralizing the fragments of lignin-containing phase and removing solvent from the neutralized fragments of lignin-containing phase to form a fragment-containing product; and
      c3) treating the fragment-containing product of step c2) with a treatment solvent and removing insoluble parts, and
   wherein the lignocellulose-containing composition and the aldehyde, boronic acid or compound selected from 2-methoxypropene, dimethyl carbonate and 2,2-dimethoxypropane are present in a weight ratio of 25:1 to 1:1, wherein the aldehyde, the boronic acid or the compound selected from 2-methoxypropene, dimethyl carbonate and 2,2-dimethoxypropane weight is based on the weight of formaldehyde.

2. The method according to claim 1, wherein step b) comprises heating the composition of step a) under acidic conditions together with an aldehyde.

3. The method according to claim 1, wherein the lignocellulose-containing composition has a lignin content of 20-40 wt. %.

4. The method according to claim 1, wherein step a) comprises suspending the lignocellulose-containing composition in an organic solvent.

5. The method according to claim 4, wherein the organic solvent is an ether containing less than 50% v/v of water.

6. The method according to claim 1, wherein step b) comprises applying a temperature of 50° C. to 120° C. for 1 to 8 hours.

7. The method according to claim 1, wherein the acidic conditions of step b) are achieved by addition of 1 to 10 mmol mineral acid per gram of the lignocellulose-containing composition.

8. The method according to claim 1, wherein the aldehyde is an aldehyde according to the formula R—COH, wherein R is an aliphatic residue with 1 to 6 carbon atoms.

9. The method according to claim 1, wherein the aldehyde is formaldehyde.

10. The method according to claim 1, wherein step c) further comprises additionally obtaining fragments of xylan.

11. The method according to claim 10, wherein the xylan fragments contain diformyl-xylose.

12. The method according to claim 1 further comprising the step:
 d) converting the fragments of lignin of step c) into monomers.

13. The method according to claim 12, wherein step d) further comprises submitting the fragments of lignin of step c) to hydrogenolysis.

14. The method according to claim 12, wherein the monomers from lignin are selected from Formulae M1 to M24:

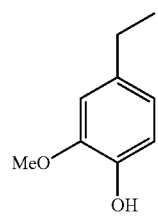

(M1)

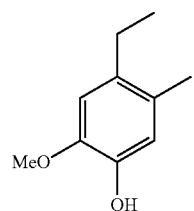

(M2)

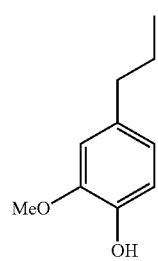

(M3)

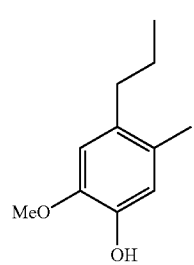

(M4)

-continued

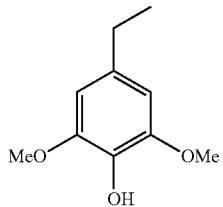

(M5)

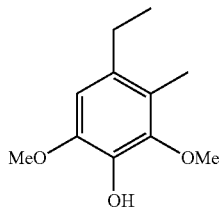

(M6)

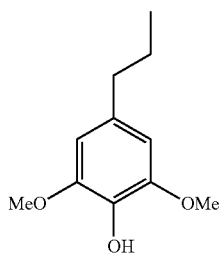

(M7)

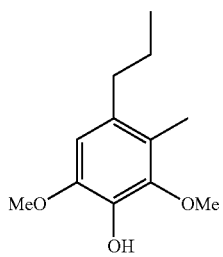

(M8)

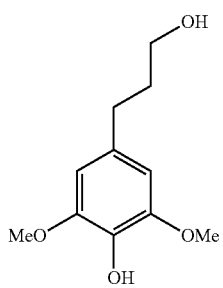 [SMILES: COc1cc(CCCO)c(C)c(OC)c1O]

(M9)

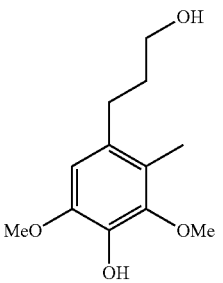

(M10)

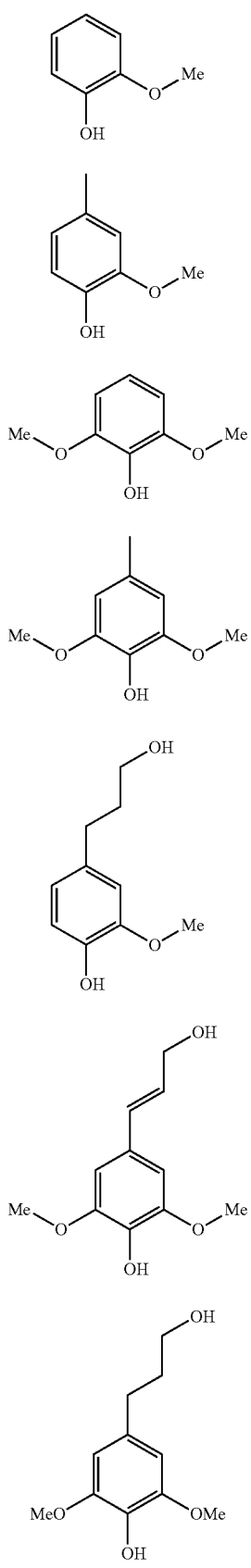
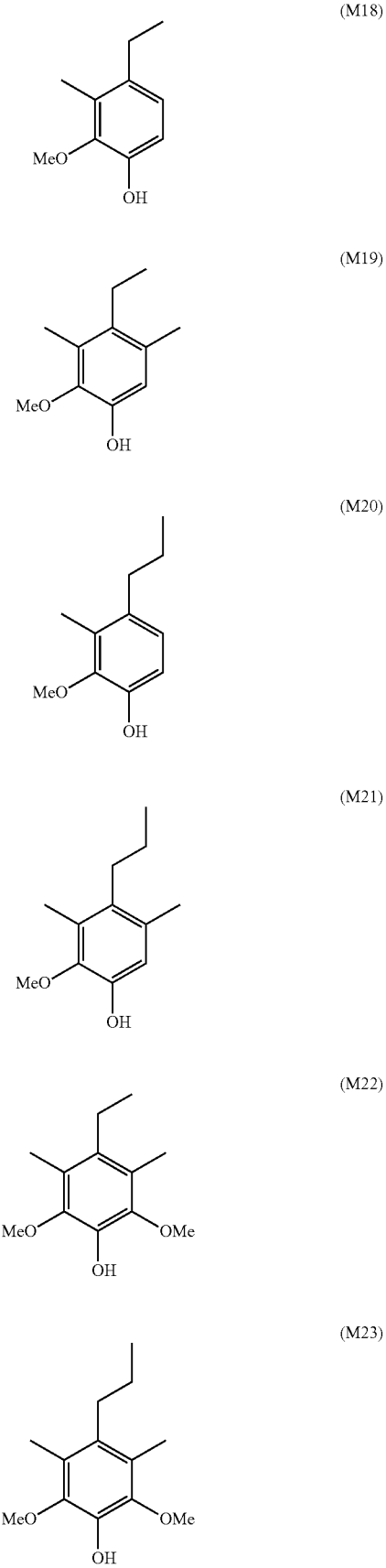

(M24)

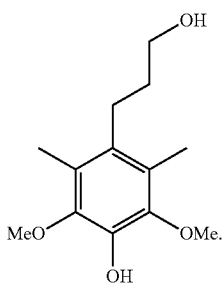

15. The method of claim 12, wherein the monomers of lignin are used for the production of resins, transportation fuels, or monomers for polymer production.

16. A method for producing fragments of xylan via depolymerization comprising the steps of:
  a) providing a lignocellulose-containing composition;
  b) heating the composition of step a) under acidic conditions together with an aldehyde, boronic acid, or a compound selected from 2-methoxypropene, dimethyl carbonate, and 2,2-dimethoxypropane; and
  c) separating fragments of xylan from the mixture of step b), wherein step c) comprises the sub-steps:
  c1) partitioning the fragments of xylan to form a fragments of xylan-containing phase and a residue;
  c2) neutralizing the fragments of xylan-containing phase and removing solvent from the neutralized fragments of xylan-containing phase to form a fragment-containing product; and
  c3) treating the fragment-containing product of step c2) with a treatment solvent and removing insoluble parts, and
wherein the lignocellulose-containing composition and the aldehyde, boronic acid or compound selected from 2-methoxypropene, dimethyl carbonate and 2,2-dimethoxypropane are present in a weight ratio of 25:1 to 1:1, wherein the aldehyde, the boronic acid or the compound selected from 2-methoxypropene, dimethyl carbonate and 2,2-dimethoxypropane weight is based on the weight of formaldehyde.

17. The method according to claim 16, wherein step b) comprises heating the composition of step a) under acidic conditions together with an aldehyde.

18. The method according to claim 17, wherein the aldehyde is formaldehyde.

* * * * *